United States Patent [19]

Guarnieri et al.

[11] Patent Number: 4,752,128
[45] Date of Patent: Jun. 21, 1988

[54] SELF-MIXING CELL FOR PHOTOMETRIC AND TURBIDIMETRIC MEASUREMENTS

[75] Inventors: Massimo Guarnieri; Marco Pacciani, Siena; Francesco Allocca, Castelnuovo Berardenga, all of Italy

[73] Assignee: Sclavo, S.p.A., Siena, Italy

[21] Appl. No.: 929,418

[22] Filed: Nov. 12, 1986

[30] Foreign Application Priority Data

Nov. 19, 1985 [IT] Italy .............................. 23882/85[U]

[51] Int. Cl.⁴ .............................................. G01N 1/10
[52] U.S. Cl. ..................................... 356/246; 356/440
[58] Field of Search ................ 356/246, 440, 447, 244

[56] References Cited

U.S. PATENT DOCUMENTS 4,229,104 10/1980 Lahme et al. ........................ 356/246
4,560,269 12/1985 Baldszun et al. .................... 356/246

Primary Examiner—Gene Wan
Assistant Examiner—Robert J. Pascal
Attorney, Agent, or Firm—Morgan & Finnegan

[57] ABSTRACT

Self-mixing cell for photometric and turbidimetric measurements, constituted by a hollow neck connected to a transparent polygonal chamber, the inner side surface of which is provided with a set of projections suitable to favor the mixing of the reactants and of the sample to be analyzed, if to the same cell an orbital or axial revolution movement is communicated. In particular, a cell is disclosed wherein the projections of the inner side surface of the chamber are the corners of a multifoil profile.

6 Claims, 2 Drawing Sheets

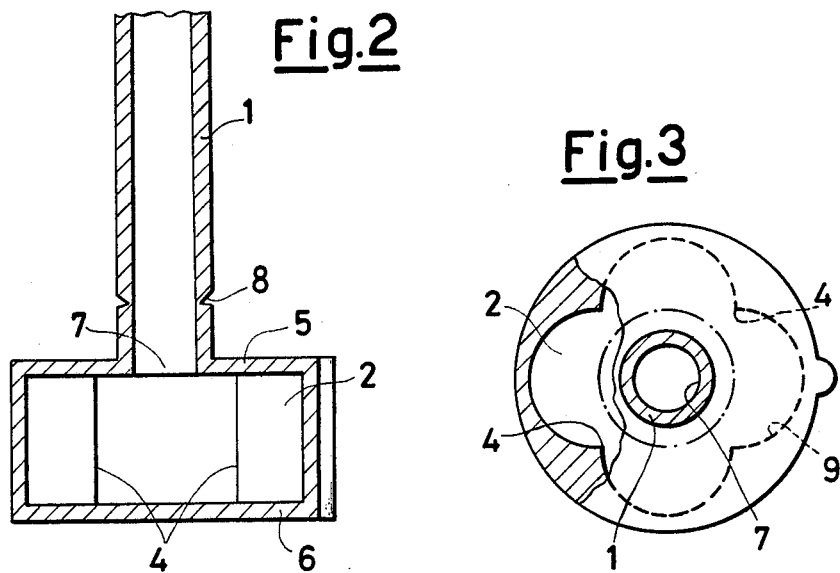
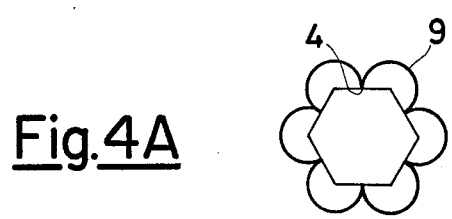
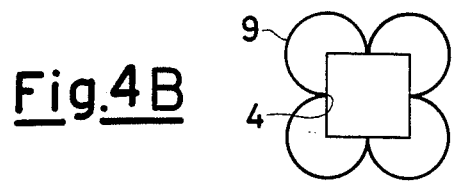
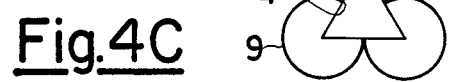

SELF-MIXING CELL FOR PHOTOMETRIC AND TURBIDIMETRIC MEASUREMENTS

FIELD OF THE INVENTION

The present invention relates to a self-mixing cell for photometric and turbidimetric measurements.

In particular, the use is disclosed of such a cell for the turbidimetric monitoring of the bacterial growth in culture broths for routine microbiological analyses: screeening, identification, bacterial sensitivity test.

BRIEF DESCRIPTION OF THE DRAWINGS

The cell shall be described with reference to the following figures:
FIG. 2=Side sectional view of the cell;
FIG. 3=Top sectional view of the cell;
FIG. 4=Examples of multifoil profile.

DETAILED DESCRIPTION OF PREFERRED EMBODIMENTS

Figure 1:
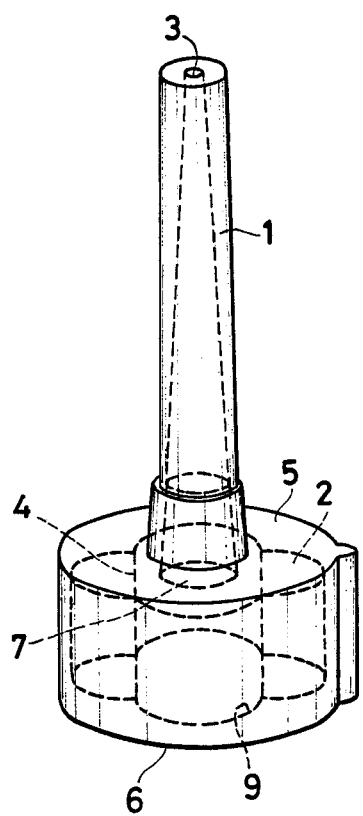
FIG. 1=Perspective view of the cell.

The cell is now described in detail, by referring to FIG. 1.

The cell consists essentially of a hollow neck (1) connected, through the opening (7), to a transparent polygonal chamber (2).

The hollow neck (1) can have variable length and shape, as a function of the instrument and analytical requirements.

A cylindrical or cone-frustum shape is generally preferred.

In case the chamber contains the necessary reactants for the analysis, the neck (1) can be closed in (3).

The closure of the neck can be accomplished by soldering a membrane having suitable characteristics of tightness to moisture and of resistance to the perforation, so to allow the direct inoculum of the sample by perforation thereof by a pipette, a syringe, etc.

The closure of the neck can be accomplished as well during the step of moulding of the cell plastic itself, or a small plug or cap can be used.

In case the closure of the cell is not accomplished by the soldering of a membrane, the same neck can be provided with a fragile pre-breakage line (8) during the moulding step.

The chamber (2) can externally be of any polygonal shapes, in FIGS. 1-3 it is of cylindrical shape.

The inner shape of the chamber, and, in particular, the profile of the inner side surface is important.

Whilst the upper inner surface (5) and the lower inner surface (6) are plane and parallel to each other, as it appears from FIG. 2, the inner side surface (9) is provided with a set of protrusions (4) suitable to favor the mixing of the reactants and of the sample. In FIGS. 1-3, a cell is exemplified, the protrusions (4) of which are the corners of a multifoil profile.

The multifoil is a plane figure, which is obtained by building arcs, external to a regular polygon, having their centers in the vertices of the polygon, and diameter equal to the polygon side.

But also derived figures are in accordance with the spirit of the present invention.

In FIG. 4 (a, b, c,) some examples of multifoil profile are shown, the profile b being the one exemplified in FIGS. 1 to 3.

The inner side surface is hence provided with corner-shaped profiles (4).

In the shape as conceived, the cell can effectively shake a corpuscular suspension, or a whatever solution, in case to it an orbital or axial revolution motion is communicated.

The bacterial suspensions, e.g., are known to be unstable, and the growing-up corpuscles tend constantly to settle.

Under the action of the rotation, the germs-containing liquid is obliged to sequentially get over the above-mentioned three of more corner-shaped protrusions: during each striding over the corner sides, a micro-vortex is created, which prevents the settlement and continuously mixes the suspension. The readability of the cell is secured in the spaces between each pair of consecutive inner protrusions.

With a corpuscolar suspension, photometric linearities of up to 500-600 digits of absorbance can be reached.

The cell can be then housed inside a support, to which a simple revolution motion is communicated.

Such a support can be, e.g., a disc of suitable material, provided with a pivot, to confer to it a revolution motion, and provided with one or more hole(s) suitable to contain the cells.

The support is then inserted inside a spectrophotometer or a turbidimeter, to carry out the measurement.

The cells not provided with protrusions on the inner side surface of their chamber must be housed inside supports, to which jumpy and/or ondulatory motions are transmitted, or which are submitted to vibration (movements more complex than a simple rotation, and more difficult to be accomplished), such motion types, on the basis of the characteristics of the sample to be analyzed, not always being sufficient to secure a perfect homogeneousness of the system.

Typical cell use fields are the clinic and industrial microbiology, with the possibility of the same to be inserted inside the most different photometric equipment, such as measurement and reaction cuvettes, being in no way limited.

In the field of the clinic microbiology, the cell of the invention can be used to carry out bacterial and cellular growths, as well as routine microbiological analyses: screening, identifications, bacterial sensitivity tests and par-tests of bacterial charges present in the various biological fluids (urine, blood, cephalorachidian fluid, etc.).

In the alimentary field, it can be used for the microbiological checks on foodstuffs and finished products (milk, meat, deep-frozen foods, etc.).

Due to the same reasons as above mentioned, applications for it can be found also in the cosmetic industry and in the pharmaceutical industry, as well as in the various toxicity tests on the most different chemical substances.

Substantially, the uses of the cell of the invention cover both the field of photometry, and that of turbibimetry.

By being a thermostatable and shakeable cell, the subject cell of the invention offers also the possibility of readout of antigen-antibody reactions in the field of immunology.

It can be used as well in the field of water turbidity analyses.

The object of the present invention is hence a self-mixing cell for photometric and turbidimetric measurements, constituted by a hollow neck connected to a transparent polygonal chamber, the inner side surface of which is provided with a set of protrusions (suitable to favor the mixing of the reactants and of the sample to be analyzed, if to the same an orbital or axial revolution motion is conferred).

The cell is of perfectly transparent material; it can be selected among the plastic materials, or any other materials fulfilling these requirements.

This is preferably selected from: polystyrene; styrene copolymers; methacrylic resins; cellulose nitrates; cellulose acetate; cellulose triacetate; cellulose esters and ethers; polyvinyl chloride; polycarbonates; polyvinyl butyrates; polyethylene; polyvinylcarbazole; glass, quartz; ureic resins.

In case, for example, the cell is used in turbidimetric measurements of the bacterial growth in culture broths for urine analysis, it shall contain all of the necessary reactants for such a measurement, and in particular:

eugonic broth for the screening and the growth curves;

test germ for the par-test;

specific reactant for the identification;

specific reactant for the bacterial sensitivity test.

The above cell can also be advantageously used for quantitative and qualitative analyses, as a container; in this case, it may also be of non-transparent material.

We claim:

1. Self-mixing cell for photometric and turbidimetric measurements, said cell being capable of mixing by rotation of the cell and by subjecting the cell to an orbital motion, said cell constituted by a hollow neck connected to a transparent chamber having a polygonal inner outline, the inner side surface of said chamber being provided with a set of protrusions.

2. Cell according to claim 1, characterized in that the protrusions of the inner side surface are the corners of a multifoil profile.

3. Cell according to claim 1, characterized in that the neck has preferably a cylinder-shape.

4. Cell according to claim 1, characterized in that the chamber has an outer outline of cylindrical shape.

5. Cell according to claim 1, characterized in that said cell is preferably constituted of materials selected from the group consisting of: polystyrene; styrene copolymers; methacrylic resins; cellulose nitrates; cellulose acetate; cellulose triacetate; cellulose esters and ethers; polyvinyl chloride; polycarbonates; polyvinyl butyrates; polyethylene; polyvinylcarbazole; glass; quartz; and ureic resins.

6. Cell according to claim 1, characterized in that the neck has preferably a cone-frustum shape.

* * * * *